United States Patent [19]

Grasselli et al.

[11] Patent Number: 5,374,410
[45] Date of Patent: Dec. 20, 1994

[54] NO$_x$ ABATEMENT PROCESS

[76] Inventors: Robert K. Grasselli, 12 Black Rock Rd., Chadds Ford, Pa. 19317-9270; Rudolph M. Lago, 633 Kings Rd., Yardley, Pa. 19067; Richard F. Socha, 42 Teaberry La., Newtown, Pa. 18940; John G. Tsikoyiannis, 191 Snowden La., Princeton, N.J. 08540

[21] Appl. No.: 148,943

[22] Filed: Nov. 8, 1993

Related U.S. Application Data

[63] Continuation-in-part of Ser. No. 910,861, Jul. 8, 1992, and a continuation-in-part of Ser. No. 47,137, Apr. 16, 1993, which is a continuation-in-part of Ser. No. 910,861, Apr. 16, 1993.

[51] Int. Cl.$^5$ ............................................ B01J 8/00
[52] U.S. Cl. .............................. 423/239.2; 502/41; 502/64; 502/71; 502/77; 423/700; 423/328.2; 208/120
[58] Field of Search .............. 423/239.2, 700, 328.2; 502/41, 64, 71, 77; 208/120

[56] References Cited

U.S. PATENT DOCUMENTS

| | | | |
|---|---|---|---|
| 3,900,554 | 8/1975 | Lyon | 423/235 |
| 4,220,632 | 9/1980 | Pence et al. | 423/239 |
| 4,771,029 | 9/1988 | Pereira et al. | 502/355 |
| 4,800,187 | 1/1989 | Lachman et al. | 502/64 |
| 4,961,917 | 10/1990 | Byrne | 423/239.2 |
| 4,980,052 | 12/1990 | Green et al. | 208/120 |
| 5,254,515 | 10/1993 | Imai | 502/64 |
| 5,260,043 | 11/1993 | Li et al. | 423/239.2 |
| 5,271,913 | 12/1993 | Iida et al. | 423/213.5 |
| 5,279,997 | 1/1994 | Montreuil et al. | 423/239.2 |

OTHER PUBLICATIONS

Lachman, I. M. et al., "Extruded Monolithic Supports", American Chemical Society Meeting, 535–543 (Aug. 1991).

*Primary Examiner*—Anthony McFarlane

[57] ABSTRACT

A process for converting noxious nitrogen oxides present in gaseous effluent to N$_2$ comprising reacting the gaseous effluent with an effective amount of reducing agent, e.g., ammonia, in the presence of a catalyst structure comprising a film of interconnected zeolite crystals bonded to a substrate, said catalyst structure being characterized by a value r representing the mg of zeolite/cm$^2$ of substrate surface and a value e representing the coating efficiency as mg of bonded zeolite/mg of YO$_2$ initially in the synthesis mixture, wherein r is at least 0.5 and e is at least 0.05.

20 Claims, 2 Drawing Sheets

$NO_x$ ABATEMENT PROCESS

CROSS-REFERENCE TO RELATED APPLICATIONS

This application is a continuation-in-part of application Ser. No. 07/910,861, filed Jul. 8, 1992, and application Ser. No. 08/047,137, filed Apr. 16, 1993, now pending, which is also a continuation-in-part of application Ser. No. 07/910,861.

FIELD OF THE INVENTION

This invention relates to a method for reducing the nitrogen oxide content of a waste gas stream. The method comprises contacting the waste gas stream with a structure comprising a zeolite film of continuously intergrown zeolite crystals strongly bonded to the surface of a substrate or monolith.

BACKGROUND OF THE INVENTION

In recent years there has been an increased concern in the United States and elsewhere about air pollution from industrial emissions of noxious oxides of nitrogen, sulfur and carbon. Government agencies, in response to such concerns, have in some cases already placed limits on allowable emissions of one or more of the pollutants, and the trend is clearly in the direction of increasingly stringent restrictions. Petroleum fuel refineries are particularly affected by present and anticipated restrictions on emissions, particularly emissions of nitrogen oxides and carbon monoxide.

Although several nitrogen oxides are known which are relatively stable at ambient conditions, it is generally recognized that two of these, viz. nitric oxide (NO) and nitrogen dioxide ($NO_2$), are the principal contributors to smog and other undesirable environmental effects when they are discharged into the atmosphere. These effects will not be discussed further here since they are well recognized.

Nitric oxide and nitrogen dioxide, under appropriate conditions, are interconvertible according to the equation $$2NO + O_2 = 2NO_2.$$

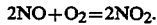

For purposes of the present invention, $NO_x$ will be used herein to represent nitric oxide, nitrogen dioxide (the principal noxious oxides of nitrogen), and/or mixtures thereof.

U.S. Pat. No. 3,900,554 describes a homogeneous gas phase thermal reaction to remove $NO_x$ from combustion effluent by adding 0.4 to 10 moles (preferably 0.5 to 1.5 moles) of ammonia followed by heating to 1600° C. to 2000° C. The $NO_x$ content is lowered as a result of its being reduced to nitrogen by reaction with ammonia. The so-called "selective catalytic reduction" (SCR) type process which operates at a much lower temperature, 200° to 600° C., is exemplified by U.S. Pat. No. 4,220,632, which describes a process for reducing $NO_x$ from a fossil fuel fired power generation plant, or from other industrial plant off-gas streams, to elemental nitrogen and/or innocuous nitrogen oxides by employing ammonia as reductant and, as catalyst, the hydrogen or sodium form of a zeolite having pore openings of about 3 to 10 Angstroms. U.S. Pat. No. 4,220,632 is incorporated herein by reference for its description of selective catalytic reduction (SCR) processes for reducing $NO_x$ emissions.

Monolithic substrates such as wash coated ceramics, described, for example, in U.S. Pat. No. 4,771,029, and extruded catalytic monoliths, described, for example, by Lachman et al., in "Extruded Monolithic Catalyst Supports," *Symposium on Catalyst Supports: Chemistry, Forming and Characteristics*, American Chemical Society, New York City Meeting, 535–543 (1991), have been described as useful in emissions control.

U.S. Pat. No. 4,800,187 describes a method for crystallizing a zeolite on the surface of a ceramic monolith containing silica with a crystallization mixture containing a ratio of $H_2O/SiO_2$ of 16–20 to 1 and a ratio of $SiO_2/Al_2O_3$ of 1 to 0.0–0.4 for the synthesis of ZSM-5. Different ratios are described for large pore zeolites X and Y.

Now it has been found that the structure of a catalyst comprising a zeolite and substrate support improves the efficacy of catalytic $NO_x$ reduction.

The catalyst structure for use herein and the method for its manufacture are novel and provide an improved $NO_x$ abatement process.

SUMMARY OF THE INVENTION

This invention provides a process for converting noxious nitrogen oxides present in oxygen-containing gaseous effluents to $N_2$ and $N_2O$ comprising reacting the gaseous effluent with an effective amount of a reducing agent, e.g., ammonia, in the presence of a catalyst structure comprising a film of interconnected zeolite crystals bonded to a substrate surface. The catalyst structure is characterized by a value r representing an amount of zeolite bonded to the substrate expressed as mg of zeolite/cm² of substrate surface, and r is at least about 0.5, preferably from about 1 to about 50.

In manufacturing the catalyst structure for use herein, a chemical mixture capable of forming the zeolite is prepared wherein the mixture comprises a $H_2O/YO_2$ molar ratio of at least about 25, Y comprising a tetravalent element, and a substrate is contacted with the mixture under crystallization conditions characterized by a value d wherein d = the ratio of $YO_2$ content of the chemical synthesis mixture to substrate superficial surface area in mg/cm²; and d is at least about 0.5 and less than about 200; preferably from about 2 to about 50;

so that an essentially continuous layer of zeolite forms as bonded to the substrate. Y is preferably silicon, germanium or titanium.

The coating efficiency, e, expressed as mg of zeolite bonded to the substrate/mg of $YO_2$ initially present in the synthesis mixture may be calculated according to the formula: e = r/d. Accordingly to the method described, e is at least about 0.05, preferably at least about 0.1 and can reach values close to 1.

The process for effecting catalytic conversion of $NO_x$ in waste, e.g., exhaust, gases involves mixing the waste gas with suitable reducing agent at up to 200° C. with a sufficient amount of reducing agent for reduction of $NO_x$, and contacting the mixture with an active form of the catalyst structure at a temperature from about 200° C. to about 600° C. Suitable reducing agents are hydrogen, CO, nitrogen-containing entities such as ammonia, hydrogen cyanide, urea and cyanuric acid, oxygenates including methanol, ethanol, propanol, formaldehyde, acetaldehyde, acetone and methyl ethyl ketone and hydrocarbons including $C_2$–$C_4$ paraffins and olefins.

Advantageously, in the catalyst structure for use herein the zeolite film is strongly bonded to the surface of a substrate so that the mechanical integrity of the film is maintained when the structure is exposed to high flow rates of gases or liquids.

DESCRIPTION OF THE PREFERRED EMBODIMENTS

The entire contents of application Ser. No. 07/910,861 are incorporated herein by reference as to description of the catalyst structure for use herein and its manufacture.

In the manufacture of the catalyst structure for use herein, a zeolite film is synthesized as bonded to a substrate. "Bonded" is intended to mean that the film is strongly adherent to the surface of a substrate and remains substantially adherent when subjected to conditions of catalysis, particularly high flow-through of gases and liquids. The film consists of an array of substantially continuously intergrown crystals which are connected to each other. This intergrowth is important for the mechanical integrity of the film.

In order to synthesize the film for the catalyst structure used in the invention, the composition of the crystallization reaction mixture has a minimum $H_2O/YO_2$ molar ratio, as calculated by conventional methods, which increases as the reaction mixture $YO_2/X_2O_3$ molar ratio decreases, Y being a tetravalent element, preferably silicon, germanium or titanium, and X being a trivalent element, preferably aluminum, iron, boron or gallium.

Figure 1:
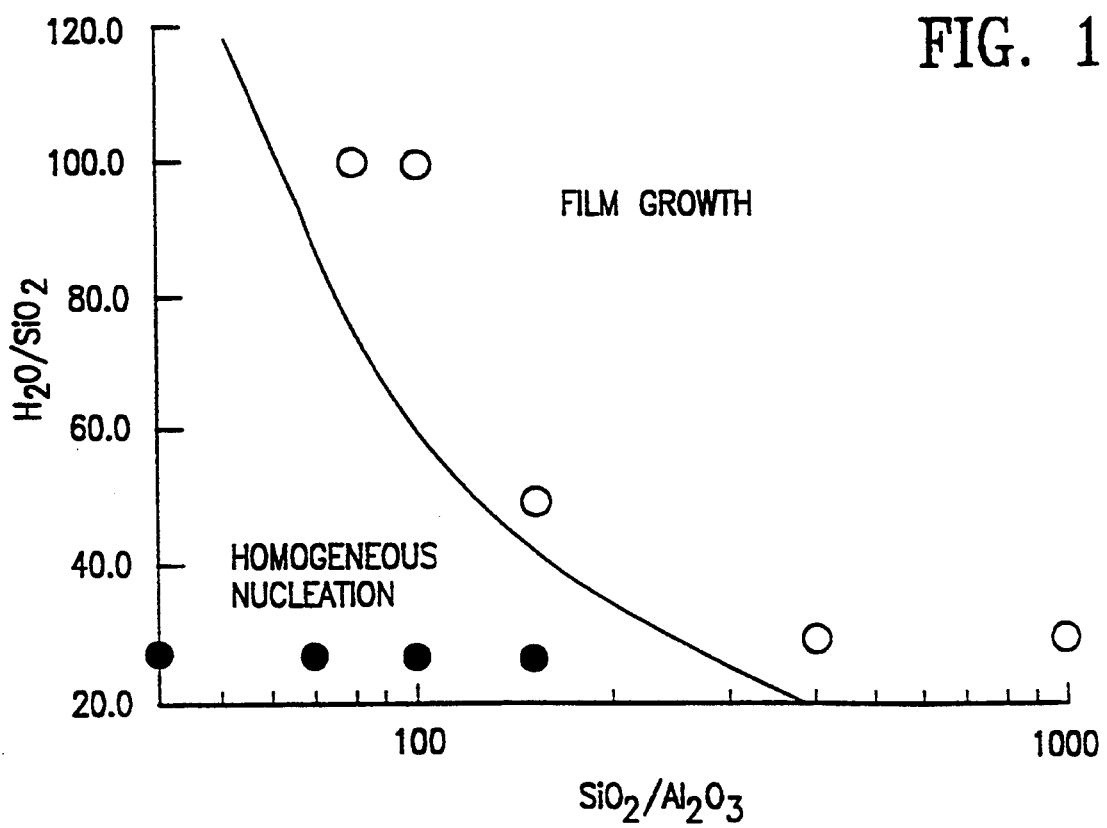
FIG. 1 is a graph demonstrating molar ratios of synthesis components for film growth.

For example, as shown in FIG. 1, in the reaction mixture, if

| $SiO_2/Al_2O_3$ | and | $H_2O/SiO_2$ |
|---|---|---|
| 1000 | | 28 |
| 400 | | 30 |
| 150 | | 50 |
| 80 | | 100 | then crystallization occurs substantially on the substrate surface and homogeneous nucleation is minimized.

However, if

| $SiO_2/Al_2O_3$ | and | $H_2O/SiO_2$ |
|---|---|---|
| 150 | | 28 |
| 100 | | 28 |
| 80 | | 28 |
| 50 | | 28 | then substantial homogeneous nucleation occurs leading to powder precipitation to the bottom of the crystallization vessel with very little zeolite adhering on the substrate.

For maximum coating efficiency, when the $YO_2/X_2O_3$ ratio in the reaction mixture is greater than about 400, the $H_2O/YO_2$ in the reaction mixture is at least about 25. When the $YO_2/X_2O_3$ is greater than about 150 and less than about 400, the $H_2O/YO_2$ is at least about 35. When the $YO_2/X_2O_3$ is less than about 150, the $H_2O/YO_2$ is at least about 45.

Accordingly, the crystallization mixture has a composition in terms of mole ratios including:

| $H_2O/YO_2$ | 25 to 500 |
|---|---|
| $YO_2/X_2O_3$ | 26 to ∞ |
| $OH^-/YO_2$ | 0.01 to 0.8 | wherein X is a trivalent element and Y is a tetravalent element.

A preferred crystallization mixture includes:

| $H_2O/YO_2$ | 30 to 200 |
|---|---|
| $YO_2/X_2O_3$ | 40 to ∞ |
| $OH^-/YO_2$ | 0.02 to 0.4 |

A more preferred crystallization mixture includes:

| $H_2O/YO_2$ | 30 to 150 |
|---|---|
| $YO_2/X_2O_3$ | 50 to ∞ |
| $OH^-/YO_2$ | 0.02 to 0.4 |

Typical zeolites to be synthesized according to this method are characterized by a Constraint Index of about 1 to about 12. The Constraint Index is a convenient measure of the extent to which a zeolite provides constrained access to molecules of varying sizes to its internal structure. The method by which Constraint Index is determined is described fully in U.S. Pat. No. 4,016,218, incorporated herein by reference for details of the method.

Zeolites which conform to the specified values of Constraint Index for medium pore zeolites include, for example, ZSM-5, ZSM-11, ZSM-12, ZSM-22, ZSM-23, ZSM-35, ZSM-38, ZSM-5/ZSM-11 intermediate, and ZSM-48, i.e., particularly zeolites which are described, for example, in U.S. Pat. Nos. 3,702,886 and Re. No. 29,948; 3,709,979; 3,832,449; 4,556,477; 4,076,842; 4,016,245; 4,046,859; 4,229,424; and 4,397,827 to which reference is made for details of these zeolites. These zeolites may be produced with differing silica:alumina ratios ranging from 12:1 upwards. They may, in fact, be produced from reaction mixtures from which aluminum is intentionally excluded, so as to produce materials having extremely high silica:alumina ratios which, in theory at least may extend up to infinity. Silica:alumina ratios of at least 30:1 and higher will be common for these zeolites, e.g., 70:1, 200:1, 500:1, 1600:1 or even higher. Highly siliceous forms of zeolites ZSM-5, ZSM-11 and ZSM-12 are described, respectively, in U.S. Pat. No. Re. 29,948 and European Patent Publication No. 14,059 to which reference is made for details of these zeolites. Also included herein is Zeolite Beta which has a Constraint Index in the range of approximately 0.6–2.0, and which is described in U.S. Pat. No. 3,308,069 and Re. No. 28,341.

Catalyst Structure Manufacture

A reaction mixture is prepared preferably containing an oxide of Y, preferably silicon, optionally a source of X, preferably aluminum, a templating agent which is an organic nitrogen containing compound, and an alkaline aqueous medium.

The sources of alkali metal oxide may be, for example, sodium, lithium, calcium, magnesium, cesium or potassium hydroxides, halides (e.g., chlorides, and bromides), sulfates, nitrates, acetates, silicates, aluminates, phosphates and salts of carboxylic acids.

The Y, e.g., silicon, oxide can be supplied from known sources such as silicates, silica hydrosol, precipitated silica hydrosol, precipitated silica, e.g., Hi-Sil, silica gel, silica acid. The X, e.g., aluminum, oxide, may be provided as only an impurity in another reactant, e.g., the Y source.

The sources of organic nitrogen-containing cations, depending, of course, on the particular zeolite product to result from crystallization from the reaction mixture, may be primary, secondary or tertiary amines or quaternary ammonium compounds. Non-limiting examples of quaternary ammonium compounds include salts of tetramethylammonium, tetraethylammonium, tetrapropylammonium, tetrabutylammonium, diethylammonium, triethylammonium, dibenzylammonium, dibenzyldimethylammonium, dibenzyldiethylammonium, benzyltrimethylammonium and chlorine. Non-limiting examples of amines useful herein include the compounds of trimethylamine, triethylamine, tripropylamine, ethylenediamine, propanediamine, butanediamine, pentanediamine, hexanediamine, methylamine, ethylamine, propylamine, butylamine, diamethylamine, diethylamine, dipropylamine, benzylamine, aniline, pyridine, piperidine and pyrrolidine.

In forming the films, a substrate is contacted with a chemical reaction mixture as described above capable of forming the desired zeolite and under crystallization conditions. After a period of time under suitable conditions, a cohesive film is formed adherent to the surface of the substrate. The orientation of the substrate surface in the reaction mixture is not critical, but it is preferably fully immersed in the synthesis solution, for a time greater than about 2 hours to about 1000 hours, preferably at least about 4.5 hours, more preferably from about 12 hours to about 120 hours; at a temperature of from about 50° C. to about 230° C., preferably from 100° C. to about 220° C.; and at a pressure from about 1 atmosphere to about 100 atmospheres, preferably from about 1 atmosphere to about 15 atmospheres.

The films are produced by synthesis under hydrothermal conditions on the substrate. Substrates contemplated to be used herein include, as non-limiting examples, metals such as Fe, Co, Ni, Sn, Ag, Pd, Pt, Cu and stainless steel, particular metals being Fe, Al, Cu, Ni and stainless steel; ceramics such as glass, clays (e.g., kaolinites, montmorillonites, and illites), quartz, mullite, titania, cordierite, zirconia, silica, alumina, spinel, carbides and nitrides (such as those of silicon, boron, zirconium, hafnium, tantalum, vanadium, molybdenum, tungsten and niobium). It is not necessary that the substrate contain silicon or aluminum.

The substrate may be an extruded monolith. Extruded monoliths of low surface area such as cordierite which may be in honeycomb shape, are advantageously used in emissions control from internal combustion engines. Other extruded monoliths of higher surface area such as titania, alumina, silica, zirconia and extruded zeolites are advantageously used in $NO_x$ emissions control such as in Selective Catalytic Reduction (SCR). Monoliths may also incorporate in their compositions, various inorganic additives such as glass particles, metal particles or diatomaceous earth.

The substrates may have various configurations. For example, the surface may be flat, curved, honeycomb shaped, layered plate form, etc.

The synthesis conditions for crystallization of a zeolite as adherent to a substrate may be further defined by a value d which is the ratio of the $YO_2$ or silica content of the synthesis hydrogel to the superficial surface area of the substrate ($mg/cm^2$). The product zeolite film-coated substrate may be characterized by the zeolite loading, i.e., the amount of zeolite adhering to the surface, a value r (mg of zeolite/$cm^2$), and by the coating efficiency e, i.e., the ratio of the amount of zeolite adhering to the substrate to the amount of silica initially present in the crystallization mixture, wherein $e = r/d$ For maximum coating efficiency, d is less than 200, preferably from about 0.5 to about 200, more preferably in the range of from about 2 to about 50; r is at least about 0.5, preferably from about 1 to about 50; and e is at least about 0.05 preferably from about 0.1 to about 1.0.

The zeolite coated substrates can be modified for a particular use by post synthesis treatment using well known techniques, in order to alter their catalytic and/or adsorption properties as desired for a particular application. For example, the structure can be steamed at a temperature of about 200° C. to 800° C. for about 1 to 50 hours. The structure can also be calcined.

Zeolites can be used either in the alkali metal form, e.g., the sodium or potassium form; the ammonium form; the hydrogen form or another univalent or multi-valent cation form. For use in this process, the catalyst structure comprising the zeolite will be subjected to thermal treatment to remove part or all of the zeolite organic constituent. Aluminum may be incorporated into the zeolite framework by treatment with aluminum halide.

The original alkali metal cations of the as synthesized zeolite can be replaced in accordance with techniques well known in the art, at least in part, by ion exchange with other cations. Preferred replacing cations include metal ions, hydrogen ions, hydrogen precursor, e.g., ammonium ions, and mixtures thereof. Particularly preferred cations are those which render the zeolite catalytically active, especially for hydrocarbon conversion. Replacing cations include hydrogen, rare earth metals and metals of Groups 3–12 of the Periodic Table of the Elements (New Notation. See, e.g., *CRC Handbook of Chemistry and Physic. S,* 69th Edition, (1988)).

A typical ion exchange technique would be to contact the synthetic zeolite with a salt of the desired replacing cation or cations. Examples of such salts includes the halides, e.g., chlorides, nitrates and sulfates.

The zeolite films described herein can be used as a catalyst in intimate combination with an oxidation-reduction component such as tungsten, vanadium, molybdenum, rhenium, copper, nickel, cobalt, chromium, manganese, or a noble metal such as platinum or palladium where a hydrogenation-dehydrogenation function is performed. Such component can be exchanged into the composition to the extent atom X, e.g., aluminum, is in the structure, impregnated in or on to it such as for example, by, in the case of platinum, treating the coated molecular sieve having ion exchange capacity with a solution containing a platinum metal-containing ion. Thus, suitable platinum compounds include chloroplatinic acid, platinum chloride, and various compounds containing the platinum amine complex.

The metal containing zeolite film structures may have essentially no acid activity, or they may have substantial acid activity to provide for dual functional catalysis. The catalytic activity of the structures can be adjusted from essentially zero to high activity, depending on the particular use thereof.

The zeolite film coated substrates for use in the present invention should usually be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing the bonded molecular sieve in a vacuum, but a longer time is required to obtain a sufficient amount of dehydration.

The zeolite coated substrate has catalytic activity for use in removing atmospheric pollutants from industrial exhaust gases.

$NO_x$ Conversion

Accordingly, the catalyst structure described above is used for selective conversion of inorganic compounds such as oxides of nitrogen ($NO_x$), for example, industrial exhaust gases and the gases formed during the oxidative regeneration of catalysts used in the processing of hydrocarbons, especially in catalytic cracking operations. The zeolite is preferably at least partly in the hydrogen form, but it may advantageously contain a minor amount of noble metal as a catalytic component, especially a metal of Periods 4, 5 and 6 and Groups 8–11 of the Periodic Table, especially Fe, Co, Ni, Cu, Rh, Pd, Ag, Ir, Pt or mixtures thereof. Amounts of metal up to about 1 weight percent are typical with lower amounts, e.g. up to about 0.1 or 0.5 weight percent being preferred.

The $NO_x$ reduction is suitably conducted by passing the gas containing the oxides of nitrogen over the catalyst at an elevated temperature, typically from at least about 200° C. to about 700° C., and usually within the range of from about 250° C. to about 600° C. The gas mixture may be mixed with a reducing agent such as, for example, ammonia to promote reduction of the oxides of nitrogen and pre-mixing may be conducted at a temperature of up to about 200° C. Gas hourly space velocity (GHSV, $hr^{-1}$) will be maintained within the range of from about 5 to about 100,000 $hr^{-1}$, usually from about 10 to about 100,000 $hr^{-1}$. The pressure of the process will be sufficient to maintain flow across the reaction zone, typically approximately atmospheric, preferably slightly above atmospheric. The amount of ammonia which is mixed with the gas mixture is shown by the equations:

$$6NO_2 + 8NH_3 = 7N_2 + 12H_2O$$

$$6NO + 4NH_3 = 5N_2 + 6H_2O$$

The $NH_3$:$NO_x$ molar ratio for the present process may be from about 0.1:1 to about 10:1, preferably from about 0.1:1 to about 1.5:1, more preferably from about 0.4:1 to about 1.1:1.

For the selective catalytic reduction (SCR) of $NO_x$ in industrial exhaust gases, the reduction proceeds approximately according to the equations (1) and (2):

$$2NO_2 + 4NH_3 + O_2 \xrightarrow{\text{catalyst}} 3N_2 + 6H_2O \quad (1)$$

$$4NO_2 + 4NH_3 + O_2 \xrightarrow{\text{catalyst}} 4N_2 + 6H_2O \quad (2)$$

The catalyst structure may also be used for the reduction of oxides of nitrogen in gaseous mixtures in the presence of other reducing agents such as carbon monoxide and hydrocarbon. Reduction of the oxides of nitrogen in this way is of particular utility in the regeneration of fluid catalytic cracking (FCC) catalysts, and in $NO_x$ emission control from automotive internal combustion engines since regeneration under appropriate conditions will produce the required concentrations of carbon monoxide and hydrocarbon which may then be used to reduce the proportion of $NO_x$ in the effluent gases in the presence of the catalyst.

FCC flue gas is typically available at about 500° C., and temperatures in this range are compatible with the present process. In contrast, conventional SCR catalysts, such as Ti—V, operate optimally at lower temperatures, e.g., 375° C. Thus, the present process requires no waste gas cooling step to effectively process hot FCC regenerator flue gas.

Coupling the flue gas outlet of an FCC regenerator with a conventional SCR process has, in the past, raised the concern that conventional SCR catalyst (e.g., Ti—V SCR catalyst which promotes oxidation) could experience dangerous thermal runaway if an operational upset in the FCC regenerator slugged unburned hydrocarbons into the FCC regenerator flue gas stream and subsequently to the SCR process. In contrast, the catalysts useful in the process of this invention are not oxidation catalysts, and therefore any thermal excursion caused by hydrocarbon slugging would be markedly less severe than with a conventional Ti—V catalyst.

The catalyst structures may also be used for the removal of both $NO_x$ and $SO_x$ from a typical flue gas stream. The removal of $SO_x$ is suitably conducted by passing the gas containing the oxides of both elements over the structure at a temperature higher than about 200° C. Premixing the flue gas stream with, for example, hydrogen promotes the reduction of the oxides of sulfur and nitrogen according to the equation:

$$SO_2 + 2NO + 5H_2 \rightarrow H_2S + N_2 + 4H_2O$$

The activity of the film is an important consideration in acid-type catalysis. Activity may be correlated with acid character. Silicious zeolites may be considered to contain $SiO_4$-tetrahedra. Substitution by a trivalent element such as aluminum introduces a negative charge which must be balanced. If this is done by a proton, the material is acidic. The charge may also be balanced by cations exchanged with alkali or alkaline earth metal cations. One measure of catalytic activity may be termed the Alpha Value. The Alpha Value is an approximate indication of the catalyst acid activity and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078, in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395 (1980).

In order to more fully illustrate the nature of the invention and the manner of practicing same, the following examples are presented.

EXAMPLES 1-8

The following substrates were prepared:
(a) Pyrex glass plate (Corning Glass Works, Corning, N.Y.) 4 cm×3 cm×0.4 cm
(b) Cordierite Monolith (Corning Glass Works, Corning, N.Y.) cylindrical, diameter=one inch height-=one inch, 100 cells/sq.inch
(c) Cordierite Monolith (Corning Glass Works, Corning, N.Y.) cylindrical, diameter=one inch height-=one inch, 400 cells/sq.inch
(d) Mullite Monolith (Corning Glass Works, Corning, N.Y.) cylindrical, diameter=one inch height-=one inch, 100 cells/sq. inch From the geometry of the monolith substrates, the surface area available for coating with zeolite was estimated to be about 170 cm$^2$ for substrates b and d and about 360 cm$^2$ for substrate c.

A synthesis hydrogel was prepared consisting of varying amounts of distilled water, NaOH, tetrapropylammonium bromide (TPABr) colloidal silica (Ludox AS-40) and NaAlO$_2$. First a solution was prepared by dissolving varying quantities of NaOH, TPABr and NaAlO$_2$ in distilled water under stirring. The colloidal silica sol was added to the basic solution and the final hydrogel stirred to produce a homogeneous solution. The substrates a, b, c, d were separately calcined in air, cooled, weighed and suspended vertically in the center of 125 ml tetrafluoroethylene (Teflon) non-stirred autoclaves so that the external surfaces of the substrates were oriented vertically. The vertical orientation was chosen to minimize gravitational deposition of homogeneously nucleated crystals (i.e., crystals not bonded to the substrate). The substrate was also not in contact with the bottom of the autoclave. The prepared synthesis hydrogel was poured into the vessel until the substrate was fully immersed, the autoclave sealed and placed inside a preheated convection oven. The autoclave was removed from the oven after a specified time period, the substrate removed from the solution, washed under flowing distilled water, dried, calcined and weighed. The weight of each substrate was higher than its weight before synthesis due to film deposition. The presence of a ZSM-5 film was confirmed by x-ray diffraction and Scanning Electron Microscopy (SEM). The results are summarized in Table I below.

In the Table, the composition of the synthesis hydrogel is defined by $SiO_2/Al_2O_3$ $H_2O/SiO_2$ $OH^-/SiO_2$ $TPABr/SiO_2$ The synthesis conditions are defined by synthesis temperature, T (°C.); crystallization time, t (days); and the ratio of the silica content of the synthesis hydrogel to the substrate superficial surface area, d (mg/cm$^2$).

The coated substrate is characterized by zeolite loading, r (mg of zeolite/cm$^2$); coating efficiency, e (mg of zeolite on substrate/mg of silica initially present in solution)

$e = r/d$

Figure 2:
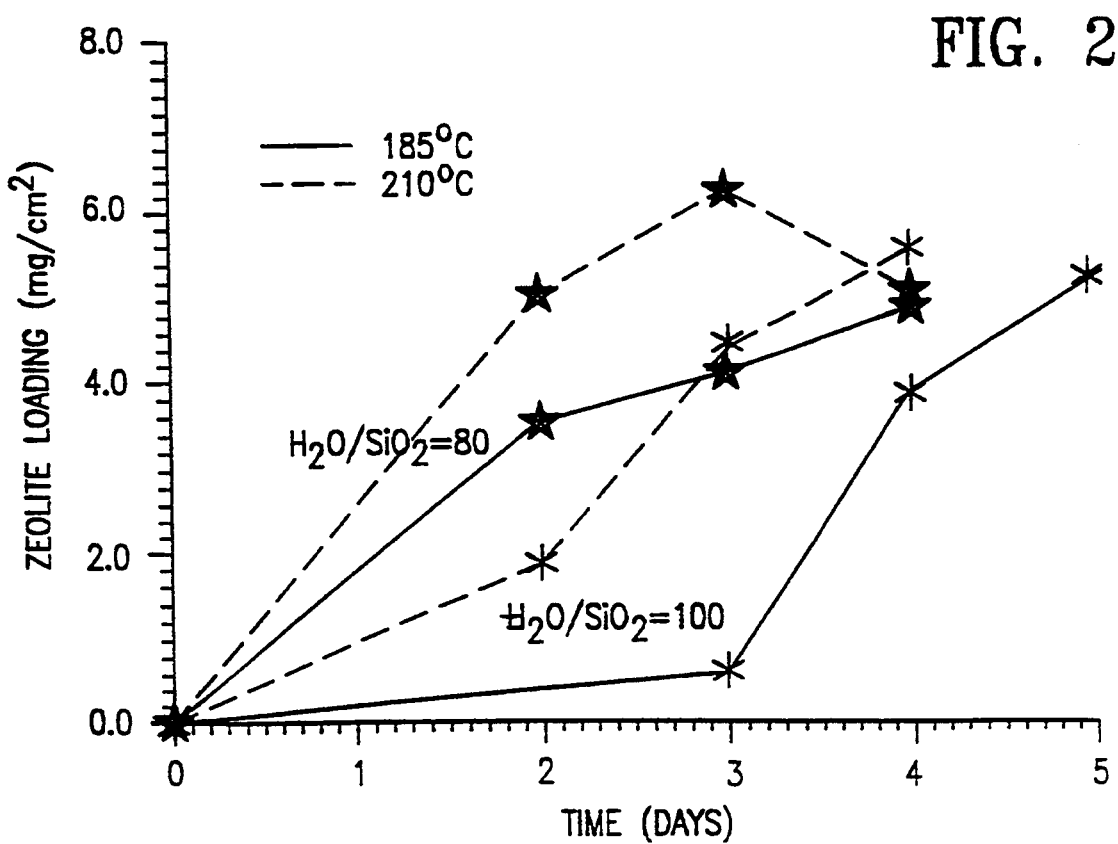
FIG. 2 is a graph representing zeolite loading on monoliths after various times at two temperatures and two $H_2O/SiO_2$ values.
Figure 3:
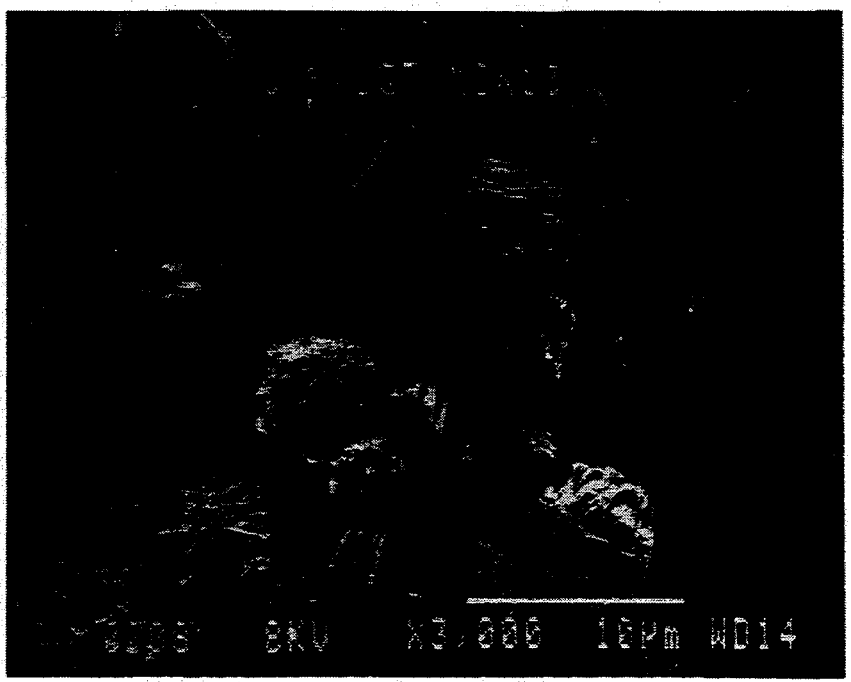
FIG. 3 is a Scanning Electronic Microscope (SEM) photomicrograph of the surface morphology of the bonded zeolite of Example 11 at 3,000 magnification.
Figure 4:
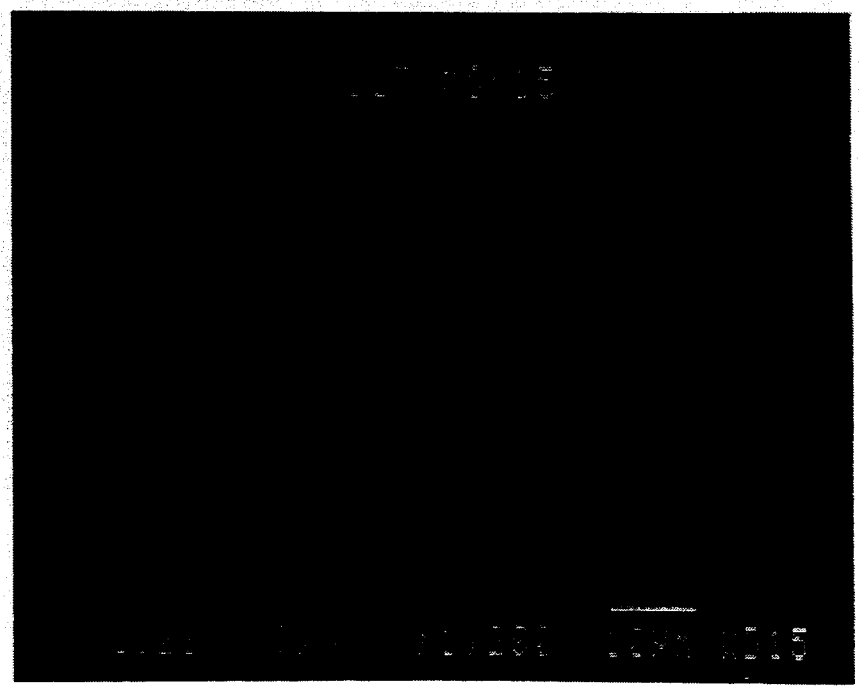
FIG. 4 is a SEM photomicrograph of the surface morphology of the bonded zeolite of Example 16 at 1,200 magnification.

The process conditions and results are summarized in Table I. Selected synthesis conditions are graphed in FIGS. 1 and 2. SEM of the films of Examples 11 and 16 is shown in FIGS. 3 and 4 respectively.

TABLE I

| Ex | $\frac{SiO_2}{Al_2O_3}$ | $\frac{H_2O}{SiO_2}$ | $\frac{OH^-}{SiO_2}$ | $\frac{TPABr}{SiO_2}$ | Subst. | T | t | d | r | e |
|---|---|---|---|---|---|---|---|---|---|---|
| 1 | ∞ | 30.0 | 0.025 | 0.055 | (a) | 180 | 3.0 | 460.0 | 46.0 | 0.10 |
| 2 | 80 | 100.0 | 0.10 | 0.10 | (a) | 180 | 5.0 | 63.0 | 15.1 | 0.24 |
| 3 | 80 | 30.0 | 0.025 | 0.055 | (a) | 180 | 3.0 | 460.0 | 0.0 | 0.00 |
| 4 | ∞ | 30.0 | 0.025 | 0.055 | (c) | 180 | 3.0 | 31.0 | 24.2 | 0.78 |
| 5 | ∞ | 30.0 | 0.025 | 0.055 | (b) | 180 | 1.0 | 18.0 | 11.5 | 0.64 |
| 6 | 400 | 30.0 | 0.025 | 0.055 | (c) | 180 | 3.0 | 31.0 | 19.5 | 0.63 |
| 7 | 150 | 50.0 | 0.065 | 0.075 | (b) | 180 | 5.0 | 32.0 | 9.6 | 0.30 |
| 8 | 100 | 100.0 | 0.10 | 0.10 | (c) | 180 | 8.0 | 8.5 | 6.55 | 0.77 |
| 9 | 100 | 100.0 | 0.10 | 0.10 | (c) | 180 | 5.0 | 50.0 | 11.0 | 0.22 |
| 10 | 100 | 100.0 | 0.10 | 0.10 | (b) | 180 | 5.0 | 95.0 | 6.65 | 0.07 |
| 11 | 100 | 100.0 | 0.10 | 0.10 | (b) | 180 | 9.0 | 16.0 | 7.36 | 0.46 |
| 12 | 100 | 100.0 | 0.10 | 0.10 | (d) | 180 | 9.0 | 16.0 | 8.64 | 0.54 |
| 13 | 80 | 100.0 | 0.10 | 0.10 | (b) | 180 | 1.7 | 16.0 | 0.48 | 0.03 |
| 14 | 80 | 100.0 | 0.10 | 0.10 | (b) | 180 | 3.0 | 16.0 | 1.12 | 0.07 |
| 15 | 80 | 100.0 | 0.10 | 0.10 | (b) | 180 | 4.0 | 16.0 | 1.60 | 0.10 |
| 16 | 80 | 100.0 | 0.10 | 0.10 | (b) | 180 | 5.0 | 16.0 | 6.40 | 0.40 |
| 17 | 80 | 100.0 | 0.10 | 0.10 | (d) | 180 | 5.0 | 16.0 | 5.76 | 0.36 |
| 18 | 80 | 20.0 | 0.10 | 0.10 | (b) | 180 | 5.0 | 40.0 | 1.20 | 0.03 |

All substrates, except in examples 3 and 18, were coated with a uniform layer of ZSM-5 which constituted from 2.4 to 179% of the substrate weight. Except for examples 3 and 18, solid particles in powder form were not observed, but only zeolite films coating the substrate and internal vessel walls were observed.

Under the conditions required here for catalyst manufacture, the weight of the zeolite film is maximized and the crystallization of homogeneously nucleated crystals is minimized. When the H$_2$O/SiO$_2$ ratio was outside the required parameters as shown in comparative example 18, homogeneously nucleated crystals which were not adherent to the substrate were formed. Furthermore, in Example 18, the zeolite loading of the monolith (r=1.2 mg/cm$^2$) and the coating efficiency (e=0.03) were much lower than the zeolite loading and coating efficiency attained under the synthesis conditions of the invention.

In general, the coating efficiency is less than 1.0 because at the end of the crystallization period, some silica may have remained in solution, coated the internal walls of the vessel or have formed homogeneously nucleated crystals which settled at the bottom of the synthetic vessel. This homogeneous nucleation is minimized under the conditions required herein.

EXAMPLE 19

Acid Activity

The acid activities of the uncoated cordierite and mullite samples were determined by the well known Alpha Test. The uncoated monoliths were found to have no acid activity (Alpha=0)

The structures of Examples 11, 15, and 16 were calcined in air at 538° C. for 6 hours, and ion exchanged according to known procedures. The Alpha values of these samples were determined to be as follows

| Example | Alpha |
|---|---|
| 11 | 44.0 |
| 15 | 4.0 |
| 16 | 27.0 |

The above data clearly demonstrate that the deposited zeolite films have appreciable acid activity.

EXAMPLE 20

Selective Catalytic Reduction (SCR) of NO with NH$_3$

The cylindrical monoliths of Examples 9 and 12 were inserted into a quartz reactor tube having an inside diameter which was about the same as the outside diameter of the monoliths. Quartz wool was used to fill around the edges to prevent gases from bypassing the monolith cells. The following table summarizes the results obtained on these materials.

| Coated Monolith | NO$_x$ Conversion, % | | |
|---|---|---|---|
|  | 350° C. | 450° C. | 550° C. |
| Ex. 9 | 28 | 41 | 62 |
| Ex. 12 | 7 | 19 | 35 |

What is claimed is:

1. A process for converting noxious nitrogen oxides present in gaseous effluent to N$_2$ comprising reacting the gaseous effluent with an effective amount of reducing agent at reaction conditions in the presence of a catalyst structure comprising a film of interconnected zeolite crystals bonded to a substrate surface, said catalyst structure having been manufactured by the method comprising contacting the substrate with a chemical reaction mixture capable of forming the zeolite film under crystallization conditions, wherein said reaction mixture comprises a H$_2$O/YO$_2$ molar ratio of at least about 25 when the YO$_2$/X$_2$O$_3$ molar ratio is greater than about 400, a H$_2$O/YO$_2$ ratio of at least about 35 when the YO$_2$/X$_2$O$_3$ ratio is greater than about 150 and less than about 400, and a H$_2$O/YO$_2$ ratio of at least about 45 when the XO$_2$/X$_2$O$_3$ ratio is less than about 150; and wherein Y is a tetravalent element and X is a trivalent element.

2. The process of claim 1 wherein said zeolite crystals have a Constraint Index of from about 1 to about 12.

3. The process of claim 1 wherein said zeolite crystals have the crystal structure of ZSM-5, ZSM-5/ZSM-11 intermediate, ZSM-11, ZSM-12, ZSM-22, ZSM-23, ZSM-35, ZSM-38, ZSM-48, or Beta.

4. The process of claim 1 wherein said zeolite crystals have the structure of ZSM-5.

5. The process of claim 1 wherein said substrate is selected from the group consisting of glass, cordierite, mullite, titania, zirconia, silica, carbides, nitrides, quartz, clay, and metals.

6. The process of claim 1 wherein said catalyst structure manufacturing method comprises steaming the zeolite at a temperature of from about 200° C. to about 800° C. for a time of from about 1 hour to about 50 hours.

7. The process of claim 1 wherein said catalyst structure manufacturing method comprises calcining the zeolite.

8. The process of claim 1 wherein said catalyst structure manufacturing method comprises ion exchanging the zeolite.

9. The process of claim 8 wherein said ion is selected from the group consisting of Pd, Pt, Ru, Mo, W, Ni, Cu, Fe, Ag, Co, Rh, V, Cr, and ammonium.

10. The process of claim 1 wherein the chemical reaction mixture has a composition in terms of mole ratios including

| H$_2$O/YO$_2$ | 25 to 500 |
|---|---|
| YO$_2$/X$_2$O$_3$ | 26 to ∞ |
| OH$^-$/YO$_2$ | 0.01 to 0.8. |

11. The process of claim 10 wherein the chemical mixture has a composition including

| H$_2$O/YO$_2$ | 30 to 200 |
|---|---|
| YO$_2$/X$_2$O$_3$ | 40 to ∞ |
| OH$^-$/YO$_2$ | 0.02 to 0.4 |

12. The process of claim 11 wherein the chemical mixture has a composition including

| H$_2$O/YO$_2$ | 30 to 150 |
|---|---|
| YO$_2$/X$_2$O$_3$ | 50 to ∞ |
| OH$^-$/YO$_2$ | 0.02 to 0.4 |

13. The process of claim 10 wherein X comprises at least one member selected from the group consisting of aluminum, boron, iron, and gallium; and Y comprises at least one member selected from the group consisting of silicon, germanium, and titanium.

14. The process of claim 13 wherein X comprises aluminum and Y comprises silicon.

15. The process of claim 1 wherein the chemical reaction mixture molar ratio of YO$_2$ to available surface area of the substrate in mg/cm$^2$ is a value d which is at least about 0.5 and less than about 200.

16. The process of claim 15 wherein d is from about 2 to about 50.

17. The process of claim 1 wherein said reaction conditions include a temperature of from about 200° C. to about 700° C. and a gas hourly space velocity of from about 5 hr$^{-1}$ to about 100,000 hr$^{-1}$.

18. The process of claim 1 wherein said reducing agent comprises ammonia.

19. The process of claim 1 wherein said gaseous effluent further comprises oxygen gas.

20. The process of claim 1 wherein said gaseous effluent further comprises $SO_2$ and hydrogen gas.

* * * * *